(12) United States Patent
Bagwan et al.

(10) Patent No.: US 10,363,019 B2
(45) Date of Patent: Jul. 30, 2019

(54) BIOPSY NEEDLE, BIOPSY NEEDLE ASSEMBLY, AND METHODS FOR BIOPSY

(71) Applicant: SECRETARY, DEPARTMENT OF BIOTECHNOLOGY, New Delhi (IN)

(72) Inventors: Siraj Bagwan, Bangalore (IN); Siddhartha Joshi, Pune (IN); Jagdish Chaturvedi, Bangalore (IN); Jonathan Pillai, Pune (IN); Pramod Garg, New Delhi (IN); Govind Makharia, New Delhi (IN); Hanish Sharma, Bhilai (IN); P.V.M. Rao, New Delhi (IN)

(73) Assignee: Secretary, Department of Biotechnology, New Delhi (IN)

( * ) Notice: Subject to any disclaimer, the term of this patent is extended or adjusted under 35 U.S.C. 154(b) by 135 days.

(21) Appl. No.: 14/760,178

(22) PCT Filed: Dec. 13, 2013

(86) PCT No.: PCT/IN2013/000768
§ 371 (c)(1),
(2) Date: Jul. 9, 2015

(87) PCT Pub. No.: WO2014/091502
PCT Pub. Date: Jun. 19, 2014

(65) Prior Publication Data
US 2016/0081674 A1      Mar. 24, 2016

(30) Foreign Application Priority Data

Dec. 14, 2012    (IN) .......................... 3881/DEL/2012

(51) Int. Cl.
A61B 10/02         (2006.01)

(52) U.S. Cl.
CPC ...... *A61B 10/0266* (2013.01); *A61B 10/0233* (2013.01); *A61B 2010/0208* (2013.01)

(58) Field of Classification Search
None
See application file for complete search history.

(56) References Cited

U.S. PATENT DOCUMENTS 4,619,272 A    10/1986  Zambelli
5,401,247 A     3/1995  Yoon
(Continued)

FOREIGN PATENT DOCUMENTS

EP    0 221 007 A1    5/1987
EP    2 163 598 A1    3/2010

OTHER PUBLICATIONS

International Preliminary Report on Patentability, dated Jan. 15, 2015, for corresponding International Application No. PCT/IN2013/000596, 25 pages.
(Continued)

*Primary Examiner* — Matthew Kremer
(74) *Attorney, Agent, or Firm* — Cozen O'Connor

(57) ABSTRACT

A biopsy needle, a biopsy needle assembly and methods to perform biopsy are disclosed. The biopsy needle includes a primary needle section formed as a hollow tube; a converging section accurately converging from a wall of the hollow tube of a first end of the primary needle section to form a piercing tip; a secondary needle section; and a body. The converging section of the biopsy needle further includes an opening on a lateral wall having a third cutting edge. The body of the biopsy needle is coupled to a second end of the primary needle section and may be coupled to an actuator to control a linear and a rotational movement of the biopsy needle.

15 Claims, 11 Drawing Sheets

(56) References Cited

U.S. PATENT DOCUMENTS

| | | | |
|---|---|---|---|
| 2001/0053873 A1* | 12/2001 | Schaaf | A61F 9/00781 600/104 |
| 2006/0116605 A1 | 6/2006 | Nakao | |
| 2006/0189891 A1* | 8/2006 | Waxman | A61B 10/0233 600/564 |
| 2006/0212060 A1* | 9/2006 | Hacker | A61B 17/320016 606/180 |
| 2008/0086142 A1* | 4/2008 | Kohm | A61B 17/3472 606/92 |
| 2008/0228104 A1 | 9/2008 | Uber et al. | |
| 2009/0283442 A1 | 11/2009 | McCall et al. | |
| 2011/0054507 A1* | 3/2011 | Batten | A61B 17/1615 606/170 |
| 2011/0072715 A1 | 3/2011 | Hanks et al. | |
| 2012/0116248 A1* | 5/2012 | McWeeney | A61B 10/0233 600/567 |

OTHER PUBLICATIONS

International Search Report, dated Jan. 15, 2014, for corresponding International Application No. PCT/IN2013/000596, 3 pages.
Written Opinion of the International Searching Authority, dated Jan. 15, 2014, for corresponding International Application No. PCT/IN2013/00596, 5 pages.
International Search Report, dated Mar. 27, 2014, for corresponding International Application No. PCT/IN2013/000768, 5 pages.
Written Opinion of the International Searching Authority, dated Mar. 27, 2014, for corresponding International Application No. PCT/IN2013/000768, 6 pages.
International Preliminary Report on Patentability, dated Jun. 16, 2015, for corresponding International Application No. PCT/IN2013/000768, 7 pages.

* cited by examiner

BIOPSY NEEDLE, BIOPSY NEEDLE ASSEMBLY, AND METHODS FOR BIOPSY

FIELD OF INVENTION

The present subject matter relates to medical devices and, particularly, to devices and methods for biopsy.

BACKGROUND

Biopsy is a medical procedure that involves taking small body tissue samples for analysis. The analysis of the body tissue sample is done in a laboratory under a microscope. Biopsies are performed to diagnose various health conditions including liver disease such as hepatitis, peptic ulcers, kidney diseases, identification of malignant or benign tumors, etc. Accordingly, biopsies may be performed on different parts of the body including liver, kidney, skin, prostrate, thyroid, brain, breast, lymph nodes and lungs.

Biopsy devices are used to perform biopsies from a biopsy region to be examined, for example, an inflicted region of a kidney of a subject. In order to extract the body tissue sample, a surgeon or a doctor first identifies a position of the biopsy region based on physical palpation, auditory auscultation, visual imaging or a combination of these techniques. Further a biopsy needle in the biopsy apparatus is moved towards the biopsy region, to remove the body tissue samples.

Different procedures of biopsies are used for different body parts or the affected tissue area. These procedures include excisional, endoscopic, and incisional biopsies. Excisional biopsy involves removal of the entire mass or abnormal area, of the body tissues. This procedure is generally used for lymph nodes or breast lumps, etc. Endoscopic biopsy uses a fiber optic endoscope to visualize and remove body cells from areas like the bladder, colon, etc. In case of the incisional or needle biopsy procedure, a special needle is used to extract tissue/cells from a body area of concern. This procedure may be used to take samples from muscles, bones and organs, such as liver or lungs.

BRIEF DESCRIPTION OF THE FIGURES

The detailed description is described with reference to the accompanying figures. In the figures, the left-most digit(s) of a reference number identifies the figure in which the reference number first appears. The same numbers are used throughout the figures to reference like features and components. Some embodiments of system and/or methods in accordance with embodiments of the present subject matter are now described, by way of example only, and with reference to the accompanying figures, in which.

DETAILED DESCRIPTION

Figure 1:
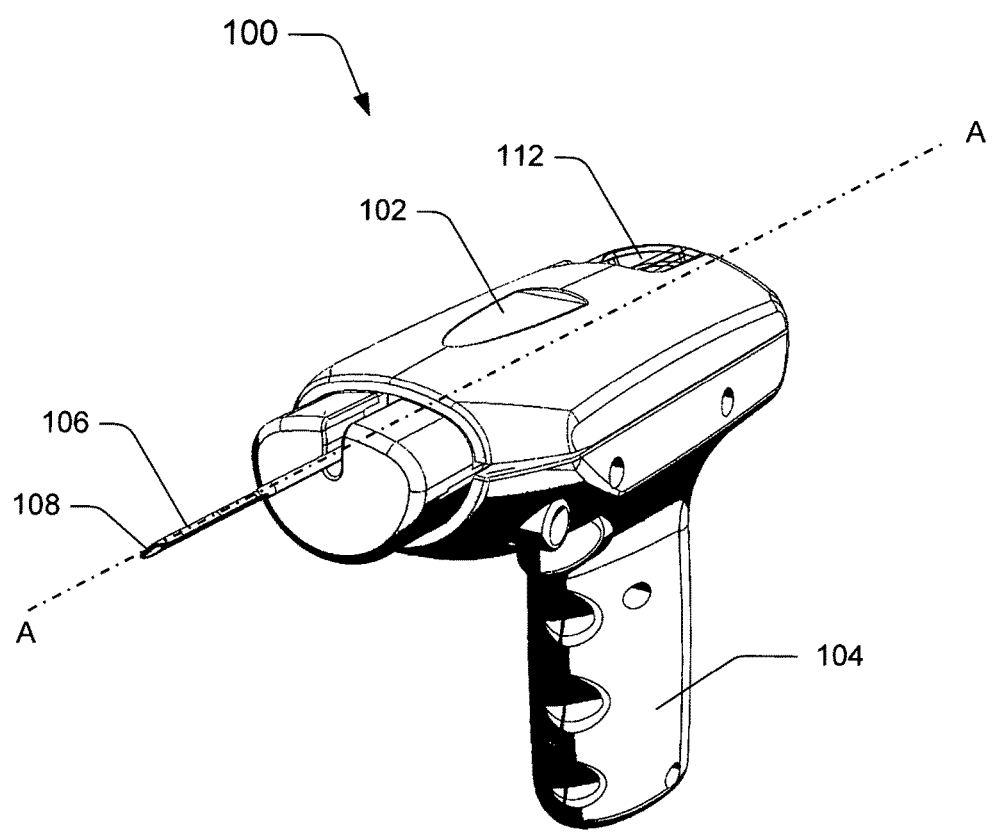
FIG. 1 illustrates various components of a biopsy device, in accordance with an embodiment of the present subject matter.

The present subject matter relates to devices and methods for biopsy, for example, for biopsy of liver.

Conventional procedures for performing biopsy include fine-needle aspiration and core needle biopsy. In fine needle aspiration biopsy, also called as Fine Needle Aspiration Cytology (FNAC), a biopsy needle is inserted into the tissue mass of concern, and a sample from the tissue mass is drawn using suction. The sample is later examined under a microscope to determine the underlying pathophysiology. However, FNAC procedure removes very small samples of tissue or cells. Therefore, this procedure is suited if the sample is predominantly fluid with only traces of solid cellular matter. However, if the tissue is solid, the small number of cells removed by the FNAC only allow for a cytological diagnosis which may lead to an incomplete assessment because the cells cannot be evaluated in relation to the surrounding tissue.

Another method of biopsy is a Core Needle Biopsy (CNB) procedure which is similar to the FNAC. In this procedure, a biopsy needle with a slightly larger diameter is used to withdraw small cylinders or cores of tissue from the area of concern. The tissue is usually cored out or cut out and a sample, usually bigger than the sample drawn by FNAC, is obtained. Further, the needle may also be inserted multiple times to get more samples and thereby obtain an accurate diagnosis. Furthermore, it is common to use a punch for making a path and inserting a needle to withdraw a sample, making it a two-step procedure, with different needles for piercing and sampling. This procedure is generally used for performing soft tissue biopsy. Usually in the CNBs, an imaging technique may be used continuously to guide the needle to the tissue that has to be cored.

In case a Menghini needle is used in CNBs, the extraction of the tissue depends on how suction is applied and on swift withdrawal of needle from the body. Therefore, in case improper suction is applied or needle is not withdrawn at an optimal speed, the tissue may get fragmented and may not be suitable for lab analysis. There may be cases where the patient is subjected to multiple samplings if the tissue sample is inadequate, or due to variability in sample quality. Further, the CNBs may also be performed with Tru-Cut® biopsy needles. A Tru-Cut® needle is a needle with an inner notched rod used to trap and excise tissue over which an outer cannula is drawn to slice the tissue into the notch. Even in the CNBs using the Tru-Cut® needle, the extracted tissue may be fragmented or inadequate. Additionally, the tissue size may be limited by the size of the notch in the rod.

Further, the FNAC and the CNB procedures may require a skilled physician, and often variation in the sample is noticed depending on the skill of the physician performing the procedure. Furthermore, tissue samples may be transferred manually to a container, which may incur the risk of exposing the physician to blood borne diseases. Also, while transferring the tissue sample, multiple components may have to be handled, such as a punch, a sampling needle, a pair of forceps for transferring and the sample container, which may result in breaking of the tissue due to mishandling and may cause procedural inconveniences and time delay.

The present matter disclosed herein describes devices and methods for performing biopsy. Although the present matter has been described with reference to biopsy device, it is to be understood by a person skilled in the art that the device disclosed herein can be altered or modified without departing from the scope of the present matter as described hereinafter.

The present subject matter relates to a biopsy needle assembly comprising a biopsy needle, to extract a tissue sample from a biopsy region, such as a liver. In an example, the biopsy needle may be either disposable or reusable. In one implementation, the biopsy needle comprises a primary needle section, formed as a hollow cylinder. Further, the primary needle section comprises a first end and a second end, where the first end of the primary needle section extends to a converging section and the second end of the primary needle section is coupled to a body of the biopsy needle. The converging section of the biopsy needle arcuately converges from walls of the hollow cylinder of the first end of the primary needle section to form a piercing tip. Such a piercing tip causes the biopsy needle to penetrate to the biopsy region of interest to extract the tissue sample. In an implementation, the piercing tip may be formed above a central axis, or along the central axis, or below the central axis, or radially offset from the central axis of the hollow cylinder.

Further, the converging section comprises an opening on the lateral wall, the opening extending from the primary needle section to the piercing tip. The opening may further form cutting edges to facilitate piercing of the biopsy needle and also to allow easy extraction of the tissue sample from the biopsy region without causing fragmentation to the adjacent tissues. In one implementation, the opening creates two cutting edges. Further, the two cutting edges may be inclined to a transverse axis of the biopsy needle, with at least two predetermined angles β and δ. In an example, the predetermined angles β and δ may be equal.

The biopsy needle may further comprise a secondary needle section, formed as a hollow cylinder, to deposit the extracted tissue sample. In an implementation, the secondary needle section may comprise an open first end that is coupled to a sample container to collect the extracted tissue sample. Further, the sample container may be detachable.

Furthermore, the secondary needle section may comprise an open second end coupled to the body of the biopsy needle. The open first end and the open second end may facilitate the movement of the extracted sample from the converging section to the sample container, based on a tissue transport mechanism. In one example, the tissue transport mechanism may employ suction. In another example, positive air pressure, or fluid flow, may be used to transport the sample into a sample chamber. In one implementation, the biopsy needle assembly may be encased in a sheath for a part or the entirety of its length. Further, in one embodiment, this sheath may be a cylindrical cannula that closely matches the external surface of the needle. The cannula may be independently connected to a source of fluid or vacuum, and may be used to deliver or extract fluid around the needle surface. The cannula may be detachably attached into the biopsy needle assembly, or may form an independent disposable component.

In one implementation, the biopsy needle assembly may further include a hand held driver unit into which the biopsy needle can be detachably coupled through the body of the biopsy needle. The hand held driver unit may further include a motor, or a set of actuators, to allow for linear and rotational movement of the primary needle section of the biopsy needle. In said implementation, the hand held driver unit may further comprise a vacuum port through which suction could be used to draw the tissue sample into a sample container. In an example, the vacuum port is integrated into the hand held driver unit. In said example, the needle is attached to the pump by means of an internally routed pipe or tubing. In another example, the vacuum port may be an independent unit, which may be connected to the hand held driver unit by a pipe or tubing.

Further, in order to generate vacuum in the vacuum port, external vacuum pump unit may be connected to the driver unit through appropriate connectors and tubing. In one example, a vacuum pump may be directly integrated into the hand held driver unit, for the purpose of generation of vacuum.

The device of the present subject matter allows for extraction and collection of the tissue sample using a biopsy needle assembly. In operation, the tissue sample is collected based on determining biopsy parameters by ultrasound or other imaging techniques. In an example, the biopsy parameters may include, but are not limited to, speed of the linear movement, speed of the rotational movement, insertion length of the primary needle section of the biopsy needle, and amount of negative pressure. The biopsy parameters may be determined based on the various techniques as understood by a person skilled in the art. Further, based of the biopsy parameters, a linear movement and a rotational movement of biopsy needle are actuated by a motor mechanism. In one example, the linear movement and rotational movement of the biopsy needle may be controlled or preprogrammed based on type of tissue present in the biopsy region. The linear movement causes the primary needle section of the biopsy needle to pierce through skin, fat and muscle and allows the biopsy needle to move from a default length to the pre-determined insertion length at a pre-determined speed for initiation of extraction of the tissue sample. Further, the tissue sample is collected into the opening of the converging section of the biopsy needle based on a suction mechanism. Once the required amount of the tissue sample is collected, the suction is withdrawn, and the biopsy needle is rotated by 90 to 360 degrees. Such a rotational movement causes a transverse cut of tissue with cutting edges, without causing fragmentation of adjacent tissue, based on the direction of rotation.

Once the sample is collected, the biopsy needle is withdrawn from the pre-determined insertion length to the default length. However, it will be understood that the biopsy needle may be withdrawn until it is completely encased in the driver unit. Further, the tissue sample is drawn from the opening of the converging section to the sample container based on the tissue transport mechanism. Once the tissue sample is drawn in to the sample container, the sample container containing the tissue sample may be detached for subsequent analysis of the tissue sample.

The described biopsy needle assembly, also referred to as a device, allows for minimal handling of components, since the extraction and collection of the tissue sample can be done with the biopsy needle assembly. Further, the described device of the present subject matter facilitates the collection of the extracted tissue sample to the sample container based on a suction mechanism. Therefore, a person performing the biopsy may not be exposed to the tissue sample and eliminates the risk of blood borne devices like Hepatitis B, Hepatitis C, and HIV. Thus the entire biopsy procedure including collection of tissue sample is executed as one procedure. Further, the biopsy needle and sample container are detachable and sterile biopsy needle and sample containers can be used as needed.

These and other advantages of the present subject matter would be described in greater detail in conjunction with the following figures. While aspects of described devices for biopsy device can be implemented in any number of different devices, environments, and/or configurations, the implementations are described in the context of the following device(s).

FIG. 1 illustrates the biopsy device 100 for performing incisional biopsy, according to embodiments of the present subject matter. The biopsy device 100 may be used predominantly for soft tissues. In one implementation, the biopsy device 100 includes a biopsy needle assembly 102 coupled to a hand held driver unit 104. The biopsy needle assembly 102 includes a biopsy needle 106 having a piercing tip 108 that causes the biopsy needle 106 to penetrate into the biopsy region of interest to extract the tissue sample. Further, the biopsy needle assembly 102 includes a cannula 110 into which the biopsy needle 106 may be coupled. In said implementation, the hand held driver unit 104 may include one or more motors (not shown) which may be coupled to the biopsy needle 106 through the biopsy needle assembly 102. Each motor of the hand held unit 104 may be configured and located in such a manner to allow longitudinal and rotational movement of the biopsy needle 106. The motors may also allow for advancement and retraction of the biopsy needle 106 along its axis, based on appropriate drive units, such as gears. In one implementation, the motors may have stepper control and may be coupled to ball screws for linear translation, or gears for rotational motion, creating the drive units to allow for independent longitudinal and rotational motion of the biopsy needle 106 along or about its axis. The axis of the biopsy needle is shown by line A-A in FIG. 1.

According to biopsy device 100 of the present subject matter, the biopsy needle 106 is multifunctional and provides for piercing, and extraction of tissue sample. Further, fragmentation of the tissue sample is avoided because of the clean longitudinal and transverse cutting action assisted by the cutting edges of the biopsy needle 106. The fluid aspirated during the extraction of the tissue sample acts as a lubricant and slides the tissue in longitudinal direction without it getting accumulated inside the needle. The biopsy needle 106 may be detachable from the biopsy needle assembly 102, and disposable.

Further the tissue sample may be collected into the sample container 112 provided at the other end of the biopsy needle assembly 102. A vacuum port (not shown) provided on the hand held driver unit 104 allows for suction of the tissue sample into the sample container 112. In one implementation, the biopsy device 100 may include a programmable control unit (not shown) to achieve repeatable, accurate, and consistent results, thereby minimizing dependence on the skill of an individual performing the biopsy.

Figure 2:
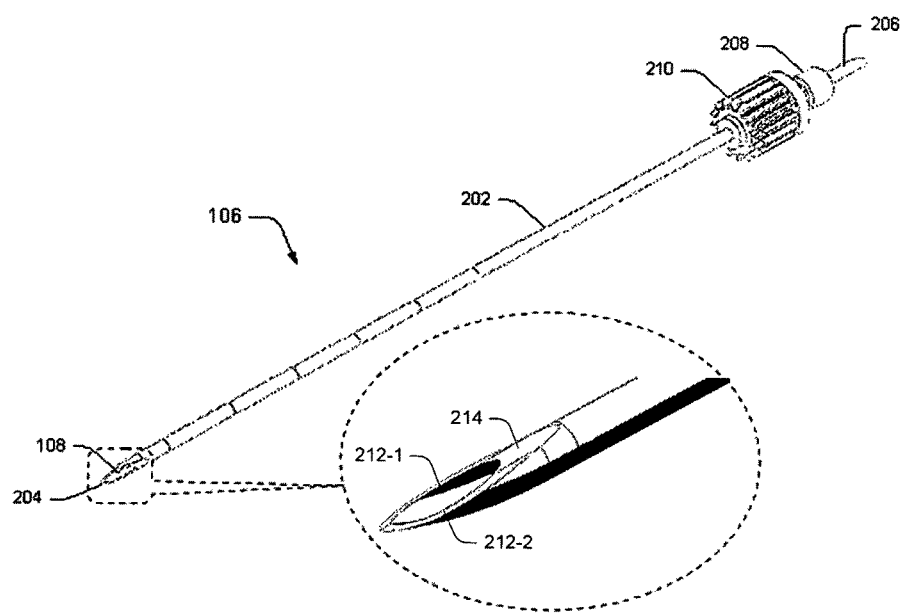
FIG. 2 illustrates an isometric view of a converging section of a biopsy needle, in accordance with an embodiment of the present subject matter.

FIG. 2 illustrates the biopsy needle 106, in accordance with an embodiment of the present subject matter. In one implementation, the biopsy needle 106 includes a primary needle section 202, a converging section 204, a secondary needle section 206, and a body 208. The primary needle section 202 and the secondary needle section 206 may be coupled together by the body 208, to form a single biopsy needle 106. The primary needle section 202 is formed as a hollow tube. Further, the primary needle section 202 comprises a first end and a second end, where the first end of the primary needle section 202 extends to the converging section 204 to extract the tissue sample, and the second end of the primary needle section 202 is coupled to the body 208 of the biopsy needle 106. In an implementation, the second end of the primary needle section 202 may be directly coupled to the sample container 112, without any intermediate connection to the body 208 or the use of a secondary needle section 206, for collection of tissue sample. In an example, the second end of the primary needle section 202 may be bevel tipped to support piercing of the second end into the sample container 112.

In one implementation, the converging section 204 includes an opening for obtaining tissue sample from the biopsy region. In said implementation, the opening may be inclined to a central axis of the biopsy needle 106 at a predetermined angle α. In an example, the predetermined angle is about 0-15 degrees above or below tangent to the top surface of the lateral opening. Such an opening may form at least one cutting edge to facilitate piercing of the biopsy needle 106 and also to allow easy extraction of the tissue sample from the biopsy region without causing fragmentation to the adjacent tissues. Further, the inclined opening forms three cutting edges, such as a first cutting edge 212-1, second cutting edge 212-2, and third cutting edge 214, on the walls of the converging section 204 to form the piercing tip 108.

In an implementation, the secondary needle section 206 of the biopsy needle 106 may be in the form of a hollow cylinder. Further, the secondary needle section 206 may include an open first end, and an open second end, where the open first end and the open second end may be of the same or unequal diameters. Further, the open first end of the secondary needle section 206 is coupled to the sample container 112 to collect the extracted tissue sample. Further, the sample container 112 may be detachable.

The open second end of the secondary needle section 206 is coupled to the body 208 of the biopsy needle 106. In an example, the open second end may be bevel tipped to support piercing of the secondary needle section 206 to the sample container 112.

In one implementation, the primary needle section 202 and the secondary needle section 206 may be of non-cylindrical cross-sections. In an example, such cross-section may include, but are not limited to elliptical, square, pentagonal and hexagonal cross-sections. It will be evident that while the overall form of the converging section 204 will remain arcuate with the walls converging to form the converging section 208, there may be differences in the location and shape of the converging section 208 as well as the cutting edges 212-1 and 212-2.

In an implementation, the biopsy needle 106 may be integrated with a gear 210 to enable rotational motion of the biopsy needle 106. For the purpose, the gear 210 may be engaged with a corresponding gear mechanism in the hand held driver unit 104, such that rotation of the gear mechanism in the hand held driver unit 104 causes the gear 210 to rotate. In one example, the gear 210 and the gear mechanism may be spur gears. In another example, the gear 210 and the gear mechanism in the hand held driver unit 104 may be helical gears. However, it will be evident that there may be alternative mechanisms to provide controlled rotational motion to the needle.

Figures 3A, 3B:
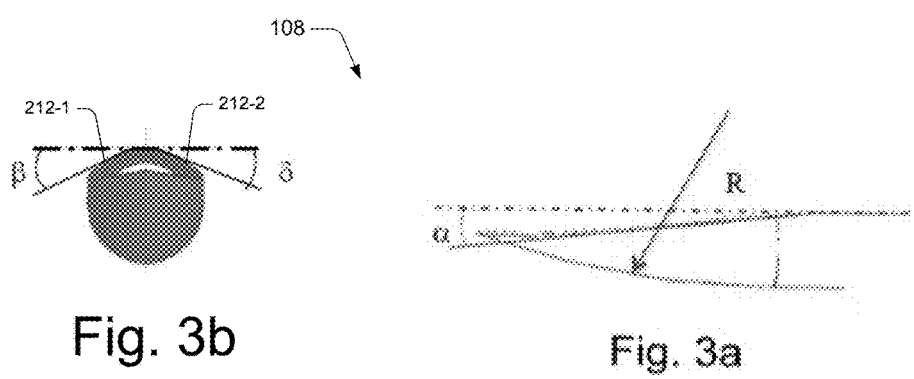
FIG. 3a illustrates a side view of the converging section of the biopsy needle, in accordance with an embodiment of the present subject matter.
FIG. 3b illustrates a front view of the converging section of the biopsy needle, in accordance with an embodiment of the present subject matter.

FIG. 3a illustrates a transverse view of the converging section 204 of the biopsy needle 106, in accordance with an embodiment of the present subject matter. In one implementation, the converging section 204 of the biopsy needle 106 may be arcuately converging from walls of the first end of the primary section 202, to form a piercing tip 108. Such a piercing tip 108 causes the biopsy needle 106 to penetrate to the biopsy region of interest in order to cut, scoop, and extract the tissue sample. In an implementation, the piercing tip 108 may be formed either above a central axis, or along a central axis or below the central axis or radially offset from the central axis of the hollow cylinder of the primary needle section 202. The arcuately converging section may include a curvature which may be defined by a radius R to provide an in-plane bend in the first end of the primary section 202. As described earlier, the primary section 202 may be a hollow cylinder. Generally, hollow cylinders are defined by inner diameter and outer diameter. In an example, the radius R may vary by a multiple of 5-15 times the value of the outer diameter of the hollow cylinder.

FIG. 3b illustrates a front view of the converging section 204 of the biopsy needle 106. Due to the predetermined angle α, the first cutting edge 212-1 and second cutting edge 212-2 are inclined to the transverse axis of the biopsy needle 106 at predetermined angles β and δ respectively. In one implementation, the predetermined angles β and δ may either equal, or unequal. In one example, the predetermined angles β and δ may be zero degrees. However, it may be understood that the predetermined angles β and δ may be independently varied to create numerous combinations of cutting edges 212-1, 212-2, and piercing tip 108, with respect to the central and transverse axes. In an example, β and δ may be varied in a range of about 0 degrees to about 90 degrees.

Further, it may be evident that the cutting edges 212-1 and 212-2 are curved (concave) as a result of a cylindrical cross-section interacting with the cutting planes defined by the combination of the angles α and β or α and δ. In case the primary section of the needle comprises of non-cylindrical cross-sections, the cutting edges 212-1 and 212-2 may be non-curvilinear. In an example, for polygonal cross-sections like square or pentagon, the cutting edges 212-1 and 212-2 may be straight. Further, by use of appropriate manufacturing techniques such as laser machining, chemical or electrochemical etching or photolithography, the cutting edges 212-2 or 212-2 may be straight, serrated or curved in a convex manner as desired.

Figure 3C:
FIG. 3c illustrates a top view of the converging section of the biopsy needle, in accordance with an embodiment of the present subject matter.

FIG. 3c illustrates a top view of the converging section 204 of the biopsy needle 106. The converging section 204 of the biopsy needle 102 facilitates the extraction of the tissue sample. In one implementation, the biopsy needle 106 can be disposable, and hence can be replaced in the biopsy needle assembly 100. Therefore, during one single procedure, multiple tissue samples can be withdrawn by changing the biopsy needle 106, as needed.

Further, the converging section 204 includes an opening on lateral wall extending from the primary needle section 202 to the piercing tip 108. The opening may further form at least one cutting edge to facilitate piercing of the biopsy needle 102 and also to allow easy extraction of the tissue sample from the biopsy region without causing fragmentation to the adjacent tissues.

Figure 4:
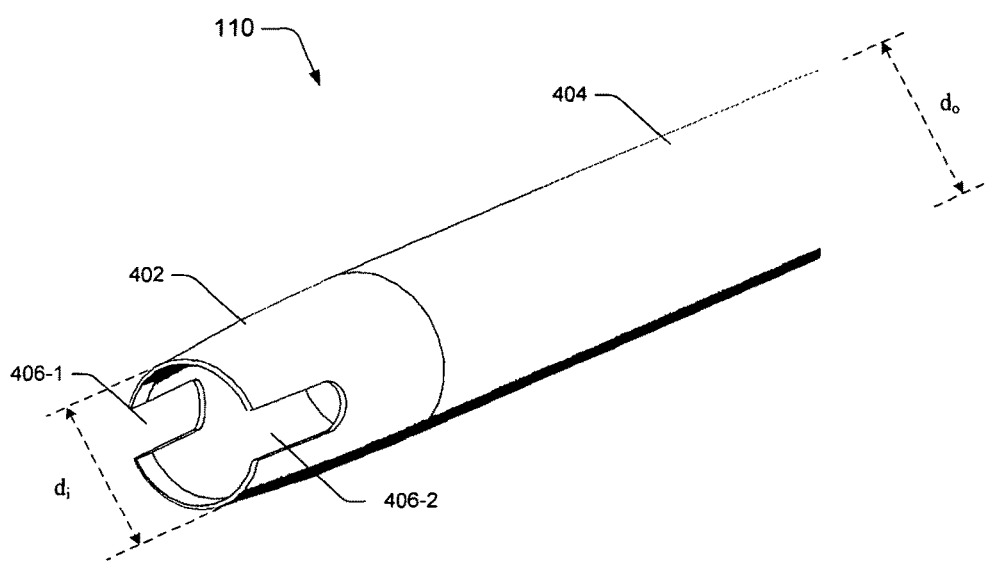
FIG. 4 illustrates a cannula, in accordance with an embodiment of the present subject matter.

FIG. 4 illustrates the cannula 110, in accordance with an embodiment of the present subject matter. In one implementation, the cannula 110 may be used as a protective sheath to the biopsy needle 106. For the purpose, the cannula 110 may be in form of a hollow tube, similar to the biopsy needle 106. In said implementation, inner diameter of the cannula 110 may be slightly greater that the outer diameter of the biopsy needle 106, so that the biopsy needle 106 is held sufficiently tight inside the cannula 110. As mentioned earlier, the biopsy needle 106 may be a hollow tube having a circular, elliptical, or polygonal cross-section. However, when the cross-section of the biopsy needle 106 is polygon, such as a square, or rectangle, or pentagon, the cross-section of the cannula 110 may remain to be circular. In such cases, the inner diameter of the cannula 110 may circumscribe the biopsy needle 106. In one implementation, the cross-section of the biopsy needle 106 and the cannula 110 may be similar. In another implementation, the cross-section of the biopsy needle 106 may be circular, and the cross-section of cannula 110 may be of various other shapes, such as square, rectangle, and the like. It will be understood that various combinations of cross-sections of the cannula 110 and the biopsy needle 106 may be implemented, such that the rotational motion of the biopsy needle 106 is not affected.

In an implementation, the cannula 110 may include a proximal end 402 with respect to the converging section 204, and a distal end 404. In one implementation, the proximal end 402 may be tapering. Further, diameters of the proximal end 402 and the distal end 404 may be indicated as $d_i$, and $d_o$, respectively. The diameter $d_o$ may vary in the range of 0.5-2 mm greater than the outer diameter of the primary needle section 202. Further, the proximal end 402 of the cannula 110 may be tapered to have a reduced diameter $d_i$ which is only slightly greater than or substantially equal to the outer diameter of the primary needle section 202. In an example, the diameter of the cannula 110 may continuously vary between $d_o$ and $d_i$.

The distal end 404 of the cannula 110 may be integrated into the biopsy needle assembly 102, and internally connected to a fluid reservoir or to a vacuum source. The cannula 110 may function as a conduit for controlled delivery of a fluid into, or aspiration of fluid out of, the biopsy region before, during, or after the biopsy procedure through openings 406-1, and 406-2, at the proximal end 402 of the cannula 110. In one example, the fluids that are delivered through cannula 110 include, but not limiting to, normal saline solution, ethanol, fibrin glue, and clotting agents.

In an implementation, the openings 406-1 and 406-2, commonly referred to as openings 406, may have one or more shapes. Further, one or more openings 406 may be provided at the proximal end 402 of the cannula 110, depending on the application. In an example, the cannula 110 may be made of a soft material, like silicone or polymer, to minimize internal injury to the tissue in the biopsy region. In an example, outer surface of the cannula 110 may be made of a hydrophilic or low-surface energy surface, to minimize friction between surface of the cannula 110 and the tissue in the biopsy region.

Figure 5:
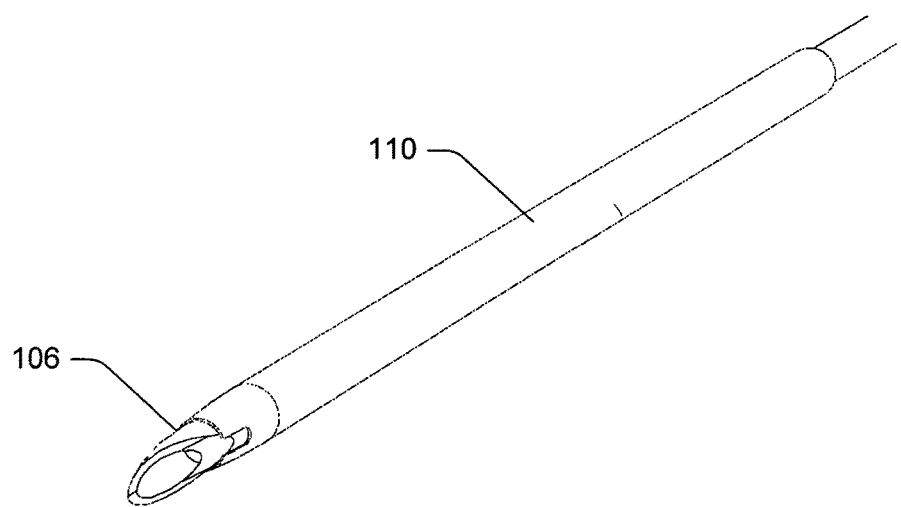
FIG. 5 illustrates an assembled view of the biopsy needle and the cannula, in accordance with an embodiment of the present subject matter.

FIG. 5 illustrates an assembled view of the cannula 110 and the biopsy needle 106. The cannula 110 may be co-axial with the biopsy needle 106, or have an axis eccentric from an axis of the biopsy needle 106. The cannula 110 may completely encompass an entire length of primary needle section 202. However, the cannula 110 may also allow the biopsy needle 106 to project out of the proximal end 402 end. The diameter $d_i$ of the proximal end 402 may be chosen so as to allow for smooth translation of the biopsy needle 106, in and out of the cannula 110.

Figure 6A:
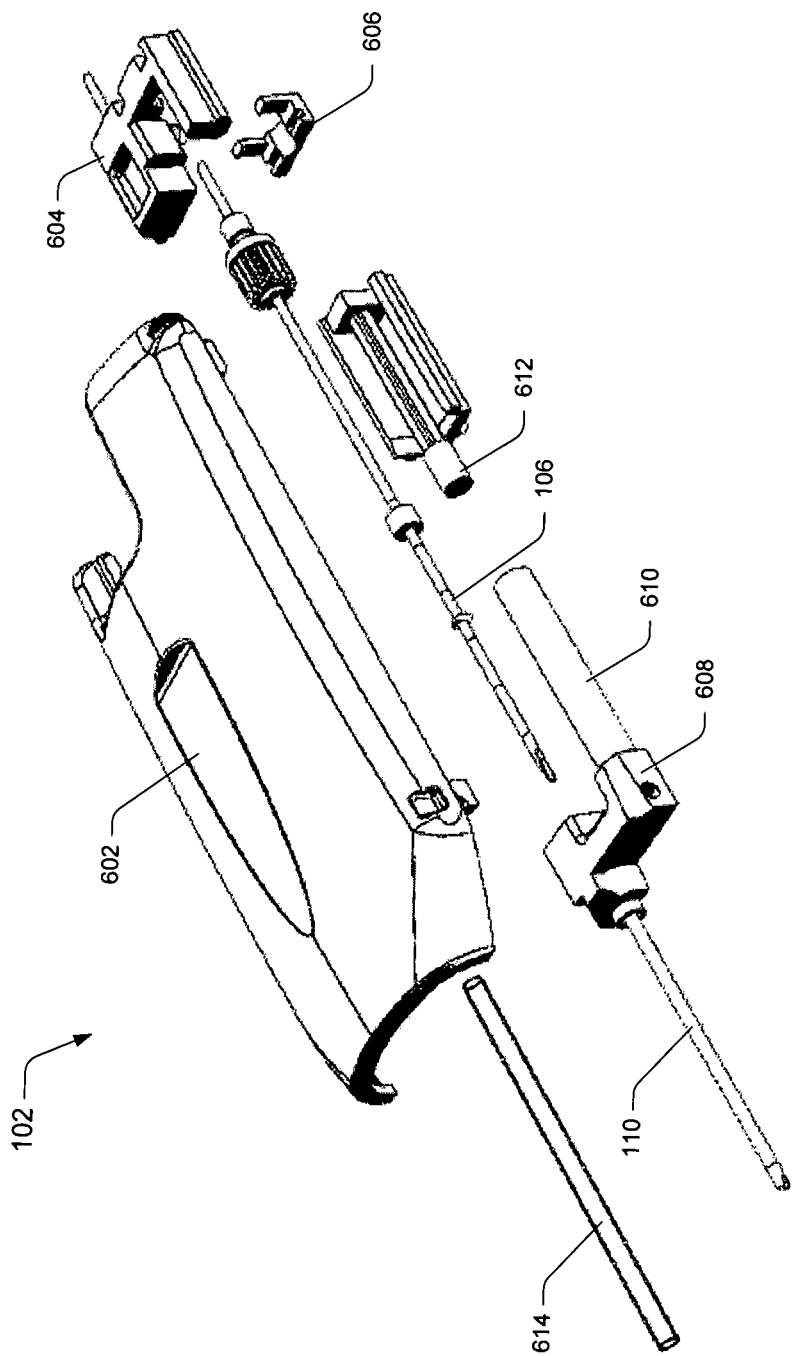
FIG. 6a illustrates an exploded view of the biopsy needle assembly, in accordance with an embodiment of the present subject matter.

FIG. 6a illustrates a top sub-assembly of the biopsy needle assembly 102, in accordance with an embodiment of the present subject matter. FIG. 6a provides an exploded view of the biopsy needle assembly 102, and illustrates sub-components included in the biopsy needle assembly 102.

In an implementation, the biopsy needle assembly 102 includes a cover 602, a first drive bracket 604, a locking pin 606, a fluid manifold 608, a fluid reservoir 610, a second drive bracket 612, and a sterile cover 614. The cover 602 may be designed in such a way that the biopsy needle 106 and the cannula 110 are free to translate along a longitudinal axis of the biopsy needle assembly 102. Further, the biopsy needle assembly may include a cavity for accommodating the sample container 112. The sample container 112 may be inserted into the cavity, by properly aligning with the cavity. The biopsy needle 106 may be engaged with a drive motor in the hand held driver unit 104 by the drive bracket 604, and may be locked into the cover 602 by the locking pin 606. The cannula 110 may be co-axially assembled with the biopsy needle 106 via the fluid manifold 608. The fluid manifold 608 provides an internal conduit for fluid flow via the cannula 110 by connecting to the fluid reservoir 610. In an example, the fluid reservoir may be a cylindrical syringe body, which may be pressurized by a piston engaged with the second drive bracket 612. The second drive bracket 612 may be independently engaged with a corresponding drive motor (not shown) in the hand held driver unit 104, such that activation of the drive motor will cause a linear translation of the first drive bracket 604 and the second drive brackets along guideways provided in the cover 602. The linear translation may either cause movement of the biopsy needle 106 or pressurization of the fluid in the fluid chamber resulting in its expulsion via the proximal end 402 of the cannula 110. The entire biopsy needle 106-cannula 110 assembly may be encased in the sterile cover 614 to ensure instrument sterility prior to use. It will be evident to a person skilled in the art that this configuration is only exemplary and there may be numerous alternative configurations that may satisfy the form and function of the biopsy needle assembly 102.

Figure 6B:
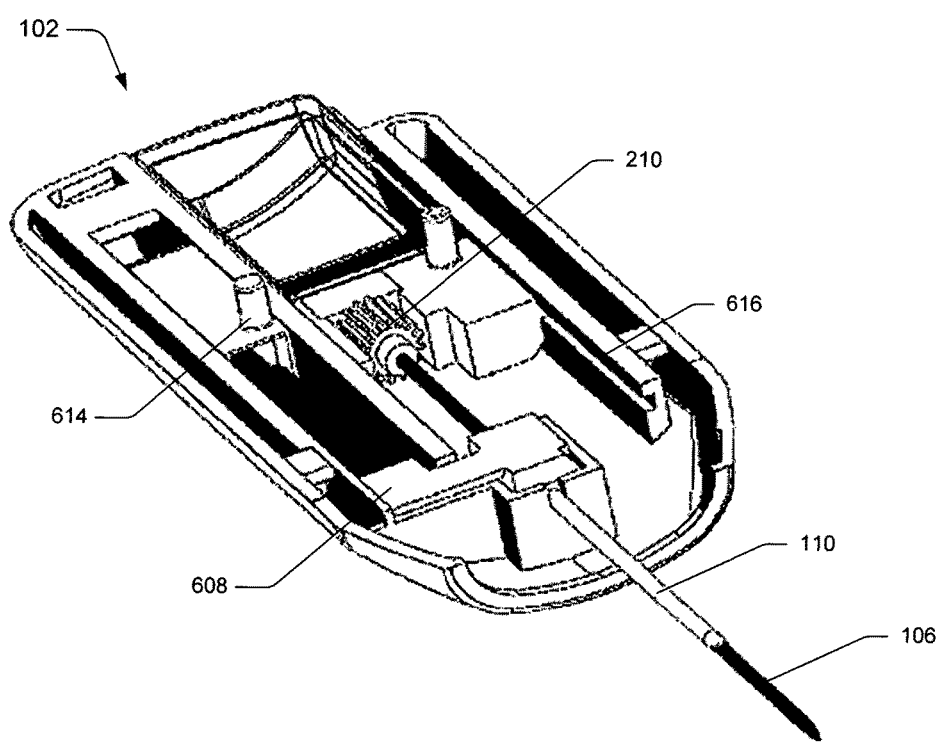
FIG. 6b illustrates a bottom view of the biopsy needle assembly, in accordance with an embodiment of the present subject matter.

FIG. 6b illustrates a bottom view of the biopsy needle assembly 102, in accordance with an embodiment of the present subject matter. In one implementation, the linear translation of the second drive brackets may be guided along the guideways 616. Further, the biopsy needle assembly 102 also includes projection 614 which couples with corresponding openings in the hand held driver unit 104, for obtaining power from motor. In said implementation, the cannula 110-biopsy needle 106 assembly may be coupled to the fluid manifold 608, such that the fluids used for aspiration may be easily passed through the cannula 110. Furthermore, the fluids as chosen by a physician may be stored in the fluid reservoir 610.

Figure 6C:
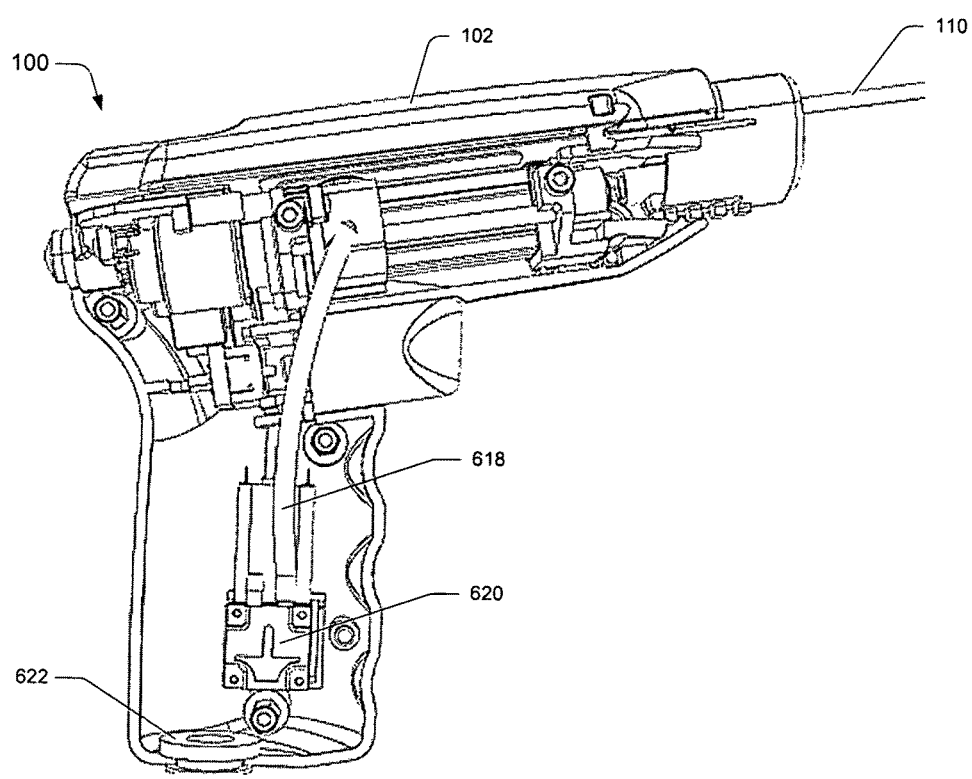
FIG. 6c illustrates a vacuum port in the biopsy needle assembly, in accordance with an embodiment of the present subject matter.

FIG. 6c illustrates a vacuum pump 620 in the biopsy needle assembly 102, in accordance with an embodiment of the present subject matter. In one implementation, the hand held driver unit 104 includes a vacuum line 618 connecting the vacuum pump 620 and the biopsy needle assembly 102. In said implementation, the vacuum pump 620 may be located in the hand held driver unit 104. In case vacuum pump is located external to the hand held driver unit 104, a vacuum port 622 may be provided at a bottom surface of the hand held driver unit 104. When the vacuum line 618 is connected to the biopsy needle 106, from the vacuum pump 620, vacuum may be generated to initiate suction of the extracted tissue sample into the sample chamber 112. As described earlier, the vacuum line 618 may also be connected to the sample container 112, in cases where the primary needle section 202 of the biopsy needle 106 is directly connected to the sample container 112.

Figure 7:
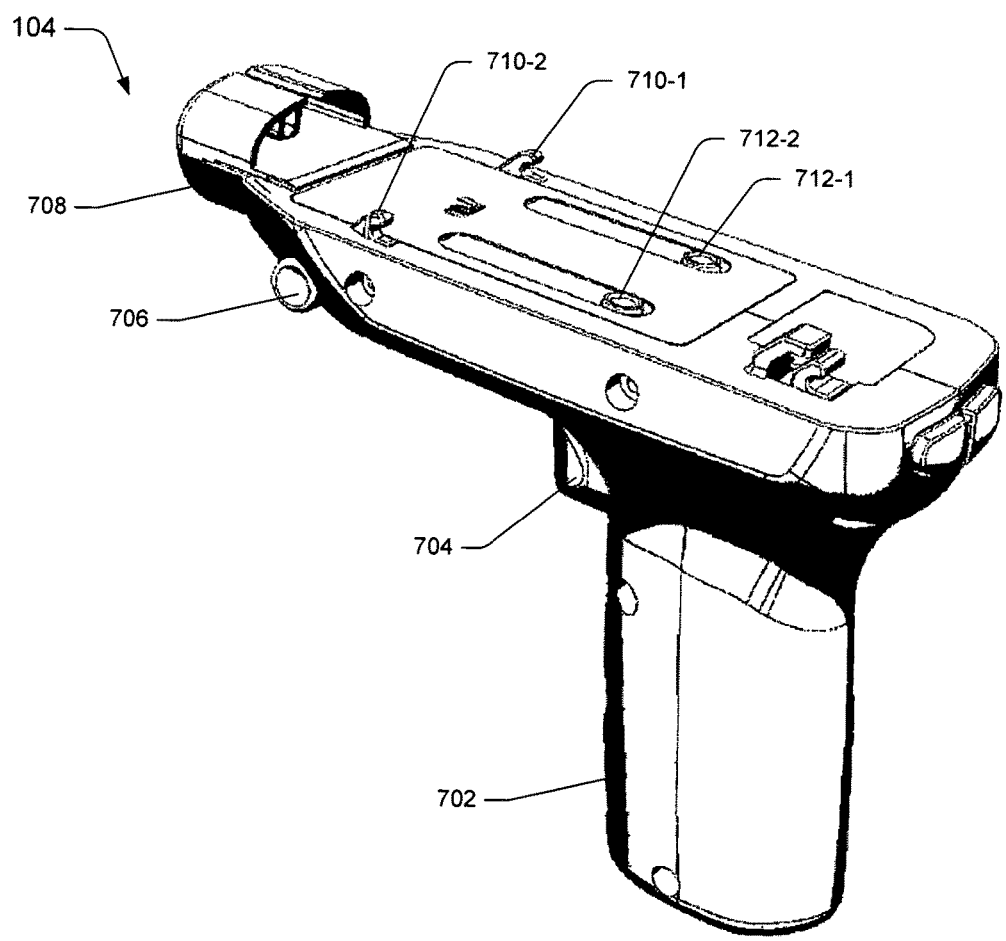
FIG. 7 illustrates a hand held driver unit, in accordance with an embodiment of the present subject matter.

FIG. 7 illustrates a perspective view of the hand held driver unit 104, in accordance with an embodiment of the present subject matter. The hand held driver unit 104 may be provided with an ergonomic grip 702, and a master button switch 704 for controlling major operations of the biopsy device 100. The front end of the hand held driver unit 104 has a stopper button 706 which may be used to pre-set the length of insertion of the biopsy needle 106, into the biopsy region, at a stopper 708. The length of the stopper 708 projecting out of the hand held driver unit 104 may be adjusted by depressing the stopper button 706. The biopsy needle assembly 102 may be engaged with the hand held driver unit 104 by appropriately engaging one or more inter-locking projections 710-1 and 710-2; and one or more motor drive units 712-1 and 712-2, with corresponding openings present in the biopsy needle assembly 102. Although the description herein mentions about engagement of the hand held driver unit 104 to the biopsy needle assembly 102 through openings, it may be understood that other methods of engagement, such as screwing, may also be used.

In one implementation, the motors in the hand held driver unit 104 may be detachably coupled to guideways 616 in the biopsy needle assembly 102 to drive and guide the biopsy needle 106. The guideways 616 may terminate in a stopper 708 that extends out from the front surface of the hand held drive unit 104, where the biopsy needle assembly 102 is coupled with the hand held unit 104. The front edge of the stopper 708 serves as a physical barrier to prevent the manual insertion of the biopsy needle 106 beyond the pre-determined insertion length. In an example, the pre-determined insertion length may be determined by measuring the distance of the biopsy region from outer surface of the skin based on utilizing ultrasound and other imaging techniques. Such techniques may be performed on the patient, prior to the biopsy procedure to identify the biopsy region of interest and to determine the pre-determined insertion length.

In one implementation, the stopper 708 may be adjustable to set the insertion length of the biopsy needle 106. The insertion length of the biopsy needle 106 may depend on factors like obesity of a person. For example, in case of obese people, a longer insertion length of biopsy needle 106 may be chosen for piercing into the body. In an undisturbed state of the biopsy device 100, the length of the biopsy needle 106 projecting out of the hand held driver unit 104 is referred to as a default length of the biopsy needle 106. Prior to the biopsy procedure, the default length may be adjusted to the pre-determined insertion length by depressing the stopper button 706 to release the stopper 708, and allowing its length to be adjusted to the pre-determined insertion length along the linear axis A-A. By releasing the stopper button 706, the stopper 708 may be locked into a position to set the default length of the primary needle section 202. The biopsy needle 106 remains fixed at its default length. However, by pressing the stopper button 706, the stopper 708 is free to move in or out. Once it is pulled out and locked at a preset length, it shields/blocks a part of the biopsy needle 106, thereby reducing its default length to the pre-set length. Once the stopper 708 is set, it protrudes out of the front of the hand held driver unit 104 up to a preset length. Hence, simple manual insertion/piercing of the biopsy needle 106 inside the body is only possible up to an extent that the biopsy needle 106 projects out ahead of the stopper 708. During insertion, once the front face of the stopper 708 rests against an external surface of the body, further insertion of the biopsy needle 106 requires automatic operation by pressing the button 704 and activating the hand held driver unit 104. In this case, the hand held driver unit 104 continues to rest against the external surface of the body supported by the stopper 708.

In one implementation, the stopper 708 is co-axial with the needle. Hence, manual insertion of the biopsy needle 106 will also advance the stopper 708 along the same axis. Insertion will stop when the front surface of the stopper 708 pushes against the external body surface. Further pushing of the biopsy needle 106 will create a reaction on the stopper 708 front surface which will depress an internal switch. The switch may be programmed to over-ride the main button 704, and initiate the same default tissue extraction as may be done by physically pressing the main button 704. In one implementation, the stopper 708 may be internally connected to a switch to actuate the motor that drives the liner translation of the biopsy needle 106. Physical pushing of the stopper 708 against the external skin surface may trigger the actuation of the motor and initiate the tissue extraction process. The motor and ball screw drive unit integrated into the hand held driver unit 104 allows for the forward and backward movement of the biopsy needle 106 at a speed which may be optimized based on identified condition of target biopsy region, as determined from apriori clinical evaluation, such as ultrasound and imaging techniques; and image based processing techniques. In one example, the image based processing techniques may include fibro scan, magnetic resonance imaging (MRI), and blood tests.

In one implementation, the hand held driver unit 104 may be fitted with a vacuum port (not shown) through which suction could be used to draw the tissue sample into the sample container 112. In said implementation, a valve (not shown) may be provided to either connect or disconnect vacuum supply from the vacuum port to the biopsy needle assembly 106.

Further, the button switch 704 located on the hand held driver unit 104 may be a multi-positional switch. The button switch 704 is used to switch the biopsy device 100 to activated mode or deactivated mode. In the activated mode, the hand held driver unit 104 can be used to translate and rotate the biopsy needle 106, about its axis, to extract the tissue sample into the biopsy needle assembly 102. When the biopsy device 100 is in deactivated mode, the hand held driver unit 104 may not be functional.

In one implementation, the biopsy needle assembly 100 may be equipped with a pre-programmed control unit (not shown) coupled to the motors and the suction mechanism to allow certain biopsy parameters to be set and used for controlling operation of the biopsy needle assembly 102. The biopsy parameters may include at least one of a speed of the linear movement, speed and extent of the rotational movement, insertion length of the primary needle section of the biopsy needle and amount of negative pressure. Therefore, the execution of the entire biopsy procedure can be controlled. The biopsy device 100 may also be fitted with a display unit (not shown) for displaying various parameters or procedural actions. In one implementation, the display unit may be integrated with the hand held driver unit 104, or may be a separate external unit in communication with the biopsy device 100. When the display unit is integrated with the hand held driver unit 104, the display unit may include a small light emitting diode (LED) display at the rear of the biopsy device 100, such that a screen of the LED display is facing a user of the biopsy device 100. In case the display unit is an external unit in communication with the biopsy device 100, the display unit may include a larger liquid crystal display (LCD) screen. In one implementation, the display unit may be adapted to receive biopsy parameters as input. In one example, the display unit integrated with the hand held driver unit 104 may be a touch screen display. In such cases, the user of the biopsy device 100 may enter the values into the biopsy device 100 through the touch screen display. When the display unit is used to control the biopsy parameters, the display unit may be referred to as a control unit. The control unit may be powered with a set of chargeable batteries housed in the assembly in one embodiment and may be connected to a suitable power source through a power chord in another embodiment. Further, the control unit may also be used to input biopsy parameters, or pre-set programs for the biopsy procedure.

Figure 8:
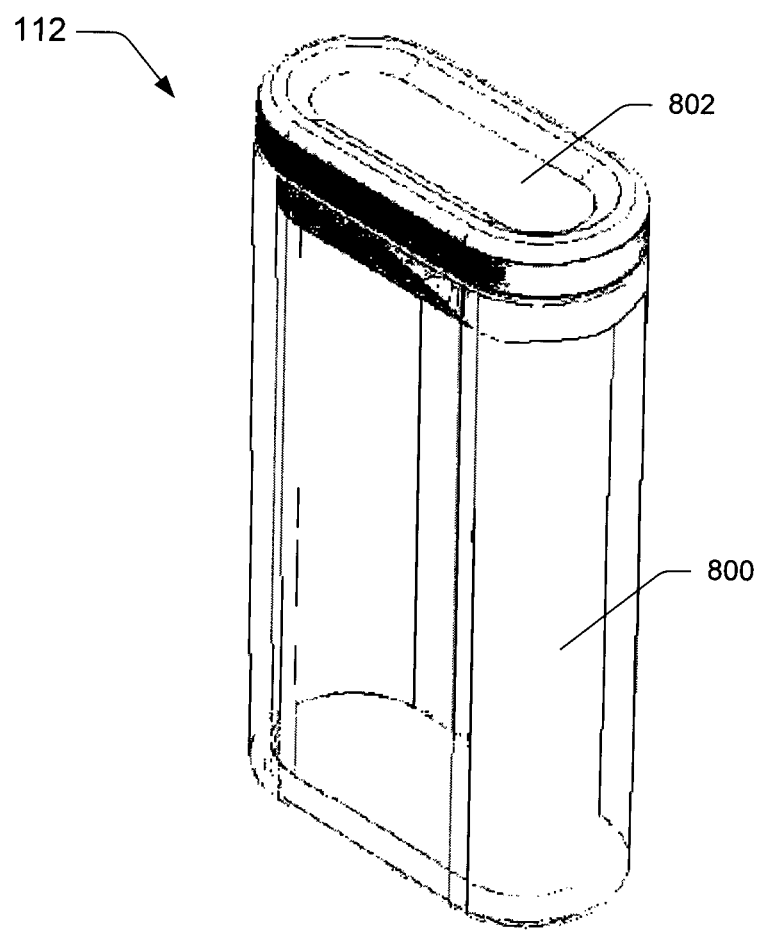
FIG. 8 illustrates a sample container of the biopsy needle assembly, in accordance with an embodiment of the present subject matter.

FIG. 8 illustrates the sample container 112, in accordance with an embodiment of the present subject matter. In one implementation, the sample container 112 includes a sample chamber 800, and a septum 802. The extracted tissue sample from the biopsy region may be collected in the sample chamber 800 for any further testing of the tissue sample. For the purpose of collecting the sample, the secondary needle section 204 may be pierced into the septum 802. In an example, the septum 802 may made of a flexible material, such as silicone, or latex, to enable easy piercing of the secondary needle section 206.

Further, the sample container 112 may be adapted to collect the extracted tissue sample based on one or more mechanisms, including suction mechanism, fluid flushing mechanism, and positive air pressure mechanism. In an implementation, the sample container 112 is coupled to the open second end of the secondary needle 206 of the biopsy needle 106. In an example, the secondary needle section 206 is bevel tipped to support piercing of the secondary needle section 206 to the sample container 112. The vacuum port of the hand held driver unit 104 may be connected to the sample chamber 112 via an independent conduit (not shown) that pierces the septum 802 at a secondary location. In an example, the sample chamber 800 may be made of transparent material, like glass, or polycarbonate plastic, to facilitate easy visualization of the collected tissue sample.

Figure 9:
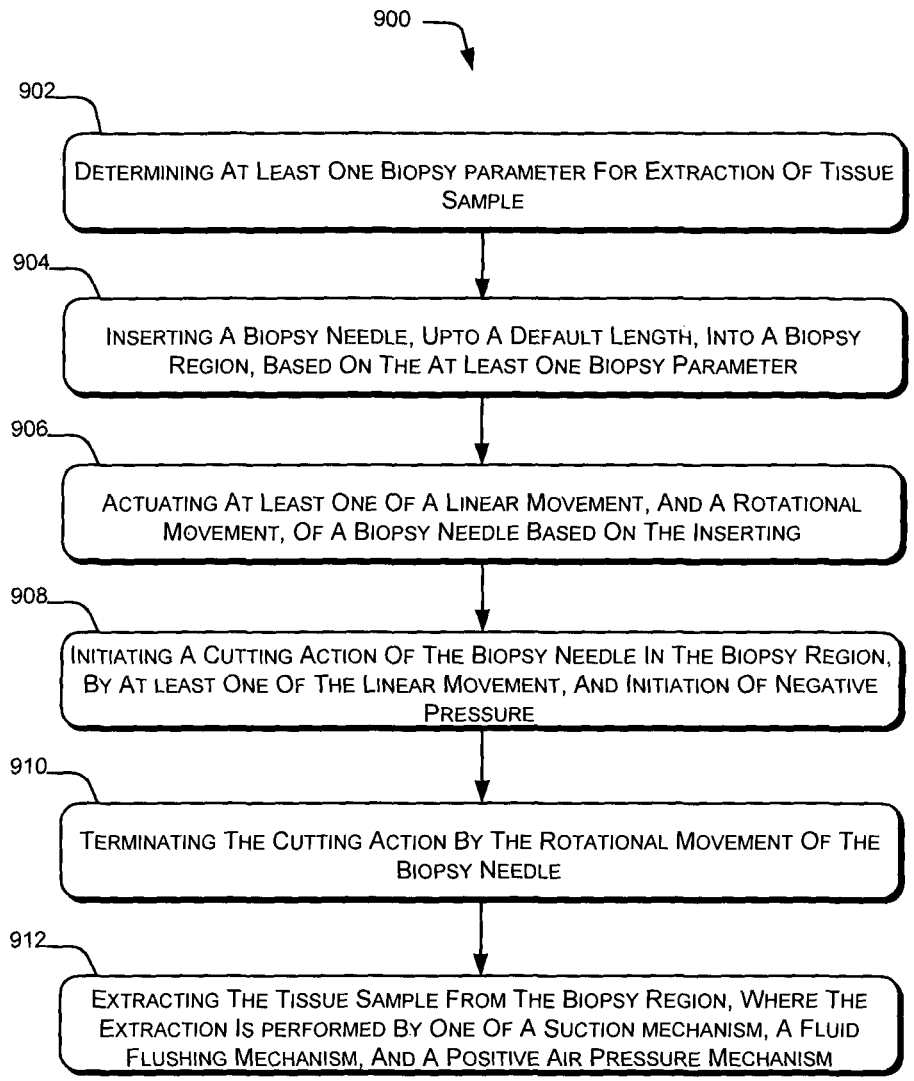
FIG. 9 illustrates a method for extracting a tissue sample from a biopsy region, according to an embodiment of the present subject matter.

FIG. 9 illustrates a method 900 for performing biopsy, in accordance with an embodiment of the present subject matter. The order in which the method 900 is described is not intended to be construed as a limitation, and any number of the described method blocks can be combined in any order to implement the method 900, or an alternative method. Additionally, individual blocks may be deleted from the method 900 without departing from the spirit and scope of the subject matter described herein. Furthermore, the method 900 can be implemented in any suitable hardware.

Referring to method 900, at block 902, at least one biopsy parameter, for the extraction of tissue sample, may be determined. In an implementation, the tissue sample is collected based on pre-determining biopsy parameters by physical palpation, auditory auscultation, imaging or a combination of these techniques. The biopsy parameters may include, but are not limited to, speed of the linear movement, speed of the rotational movement, insertion length of the primary needle section 202 of the biopsy needle 106 and intensity of negative pressure.

At block 904, a biopsy needle 106 may be inserted, up to a default length, into a biopsy region, based on the at least one biopsy parameter. In one implementation, the biopsy region, close to a target organ, such as the liver, may be located and marked on a surface of the body. Based on the depth of the target organ, and at least one biopsy parameter, the default length of the biopsy needle 106 may be set using a stopper button 706 and stopper 708. In an example, such setting of the default length may be done manually by pushing the converging tip 204 of the biopsy needle 106 through skin, fat, and muscle tissue. The converging tip 204 is able to cleave the external tissue without allowing any tissue to enter a lumen of the biopsy needle 106. In such mode, the biopsy needle 106 functions as a trocar to create a path to the target organ. The stopper 708 physically limits the entry of the primary needle section 202 beyond a preset de-fault length. In an alternative example, the entire process of piercing through the external surface of skin, fat and abdominal tissue, as well as piercing the target organ, may be completely automated by pressing the main button 704 of the hand held driver unit 104.

At block 906, at least one of a linear movement, and a rotational movement, of a biopsy needle 106 may be actuated based on the at least one biopsy parameter. Once the biopsy needle 106 is set to the default length, and inserted into the marked biopsy region, the linear movement of biopsy needle 106, within the target organ, may be actuated based on the pre-determined biopsy parameters. In an example, the linear movement is actuated by a motor that causes the primary needle section 202 of the biopsy needle 106 to move from the default length to a pre-determined insertion length, at a pre-determined speed for initiation of extraction of the tissue sample. Such an actuation is facilitated by the depression of the main button 704, with the simultaneous initiation of a pre-determined intensity of negative pressure (suction) inside the biopsy needle 106.

At block 908, a cutting action of the biopsy needle 106, in the biopsy region, may be initiated by at least one of a linear movement, and initiation of negative pressure. In one implementation, combined action of suction and the linear movement may cause collection of the tissue sample, from the biopsy region, via a scooping action, into a lateral opening in the converging section 204 of the biopsy needle 106. As the tissue sample is collected into the converging section 204, due to the suction, it may be cleaved from surrounding tissue by the cutting action initiated by the cutting edges 212-1, 212-2, and 214. The converging section 204 and the cutting edges 212-1, 212-2, and 214 therefore act in tandem to direct and cut the tissue sample into the lateral opening of the biopsy needle 106. Such combination of suction and linear movement may result in a cleanly cut tissue sample, or a cylindrical sample of tissue, being collected inside a lumen of the primary needle section 202 of the biopsy needle 106.

At block 910, the cutting action may be terminated by the rotational movement of the biopsy needle 106. In one implementation, the main button 704 may be depressed further to withdraw the suction from the biopsy needle 106. In said implementation, the depression of the main button 704 may simultaneously initiate a controlled rotational movement of the biopsy needle 106 to collect a desired amount of the tissue sample from the biopsy region. In one example, the controlled rotation may include a rate of rotation of the biopsy needle 106 about the axis A-A, and a pre-defined angular displacement. Such a controlled rotational movement may allow termination of tissue sample collection by causing a transverse cut at by the cutting edges 212-1, or 212-2, depending on the direction of rotation, without causing fragmentation to adjacent tissues or disruption of the tissue core. It will be understood that the rotational motion of the needle may initiated independently from its translational motion. In one implementation, the rotational motion of the biopsy needle 106 may be combined with the translational motion, such that a complex three dimensional path may be traced by the converging end 204 of the biopsy needle 106 in the biopsy region.

At block 912, the tissue sample may be extracted from the biopsy region, where the extraction is performed by one of a suction mechanism, a fluid flushing mechanism, and a positive air pressure mechanism. In an implementation, the tissue sample may be automatically transported through the lumen of the primary needle section 202 into the sample chamber 112. In an example, such transport of the tissue sample may be achieved by re-activating application of suction at a pre-determined intensity, and for a pre-determined duration, to allow for deposition of the tissue sample into the sample chamber 112.

For the purpose of re-activating the suction, the main button 704 may be depressed further. Once the tissue sample is drawn in to the sample container 112, the sample container 112 may be detached for subsequent analysis of the tissue sample. The sample container 112 can be replaced on the biopsy needle assembly 102 for further tissue extraction. In an example, the sample container 112 may be replaced each time the biopsy needle assembly 102 is used for extraction of a new tissue sample.

Once the sample is collected in the sample container 112, the biopsy needle 106 may be withdrawn from the pre-determined insertion length to the default length of the biopsy needle 106, leaving the cannula 110 inside the biopsy region. In case the person performing the biopsy determines that the tissue sample collected in the sample container 112 is not adequate, then a second sample may be extracted from the same biopsy region. In an example, this may be achieved by pressing the main button 704 twice in quick succession.

Although the disclosed subject matter has been described in language specific to structural features and/or methods, it is to be understood that the appended claims are not necessarily limited to the specific features or methods described. Rather, the specific features are disclosed as exemplary embodiments of the biopsy needle assembly.

We claim:

1. A biopsy needle to pierce a biopsy region and extract a tissue sample, the biopsy needle comprising:
   a primary needle section formed as a hollow tube, wherein the primary needle section comprises a first end and a second end; and
   a converging section arcuately converging from a wall of the hollow tube of the first end to form a piercing tip, wherein the converging section comprises a first cutting edge and a second cutting edge that converge arcuately for piercing the biopsy region, and wherein the converging section comprises an opening on a lateral wall extending from the wall of the primary needle section to the piercing tip, the opening having a third cutting edge for cutting the tissue sample under application of a negative pressure,
   wherein the opening is inclined at a predetermined angle $\alpha$ ranging from an angle greater than 0 degrees to an angle of 15 degrees to a central axis of the biopsy needle, and wherein the first cutting edge is inclined to a transverse axis of the biopsy needle at a predetermined angle β ranging from an angle greater than 0 degrees to an angle of 30 degrees, and the second edge is inclined to the transverse axis of the biopsy needle at a predetermined angle δ ranging from an angle greater than 0 degrees to an angle of 30 degrees, and wherein a surface of at least one of the first cutting edge, the second cutting edge, and the third cutting edge is curved, and wherein the converging section includes a curvature defined by a radius R, the radius R being in a range of 5-15 times of an outer diameter of the primary needle section to provide an in-plane bend that spans across the opening, the in-plane bend extending below the opening from the piercing tip to the wall of the primary needle section, whereby the piercing tip is positioned above the central axis of the biopsy needle.

2. A biopsy needle assembly comprising:
a biopsy needle to extract a tissue sample, wherein the biopsy needle comprises:
  a primary needle section formed as a hollow tube, wherein the primary needle section comprises a first end and a second end; and
  a converging section arcuately converging from a wall of the hollow tube of the first end to form a piercing tip, wherein the converging section comprises a first cutting edge and a second cutting edge that converge arcuately for piercing a biopsy region, and wherein the converging section comprises an opening having a third cutting edge for cutting the tissue sample under application of a negative pressure, wherein the opening is inclined at a predetermined angle α ranging from an angle greater than 0 degrees to an angle of 15 degrees to a central axis of the biopsy needle, and wherein the first cutting edge is inclined to a transverse axis of the biopsy needle at a predetermined angle β ranging from an angle greater than 0 degrees to an angle of 30 degrees, and the second cutting edge is inclined to the transverse axis of the biopsy needle at a predetermined angle δ ranging from an angle greater than 0 degrees to an angle of 30 degrees, and wherein the converging section includes a curvature defined by a radius R, the radius R being in a range of 5-15 times of an outer diameter of the primary needle section to provide an in-plane bend that spans across the opening, the in-plane bend extending from the piercing tip to the wall of the primary needle section, whereby the piercing tip is positioned above the central axis of the biopsy needle;
  a body coupled to the second end of the primary needle section, wherein the body is coupled to an actuator to control a linear movement and a rotational movement of the biopsy needle to pierce the biopsy region; and
  a suction mechanism for applying the negative pressure through the biopsy needle on a target tissue for cutting the tissue sample by the third cutting edge.

3. The biopsy needle assembly as claimed in claim 2, wherein a cross-section of the hollow tube is one of a circle, an ellipse, and a polygon.

4. The biopsy needle assembly as claimed in claim 2, wherein the body is coupled to a secondary needle section of the biopsy needle assembly.

5. The biopsy needle assembly as claimed in claim 4, wherein the secondary needle section is formed as a hollow tube, and wherein the secondary needle section comprises a first end coupled to a sample container.

6. The biopsy needle assembly as claimed in claim 5, wherein the extracted tissue sample is collected in the sample container based on one of the suction mechanism and a fluid flushing mechanism.

7. The biopsy needle assembly as claimed in claim 2, wherein the opening extends from the wall of the hollow tube to the piercing tip.

8. The biopsy needle assembly as claimed in claim 2 further comprising a hand held driver unit, wherein the biopsy needle is detachably coupled with the hand held driver unit.

9. The biopsy needle assembly as claimed in claim 8, wherein the actuator comprises at least one of: a motor and a gear mechanism coupled to the hand held driver unit to cause the linear movement or the rotational movement of the biopsy needle based on at least one biopsy parameter.

10. A method to collect a tissue sample, the method comprising:
determining at least one biopsy parameter for extraction of the tissue sample;
actuating a linear movement of a biopsy needle based on the at least one biopsy parameter, wherein the linear movement causes the biopsy needle to enter a biopsy region to extract the tissue sample, the biopsy needle comprising:
  a primary needle section formed as a hollow tube; and
  a converging section arcuately converging to form a piercing tip, wherein the converging section comprises a first cutting edge and a second cutting edge that converge arcuately for piercing the biopsy region, and wherein the converging section comprises an opening having a third cutting edge for cutting the tissue sample under application of a negative pressure, wherein the opening is inclined at a predetermined angle α ranging from an angle greater than 0 degrees to an angle of 15 degrees to a central axis of the biopsy needle, and wherein the first cutting edge is inclined to a transverse axis of the biopsy needle at a predetermined angle β ranging from an angle greater than 0 degrees to an angle of 30 degrees, and the second edge is inclined to the transverse axis of the biopsy needle at a predetermined angle δ ranging from an angle greater than 0 degrees to an angle of 30 degrees, and
wherein the converging section includes a curvature defined by a radius R, the radius R being in a range of 5-15 times of an outer diameter of the primary needle section to provide an in-plane bend that spans across the opening, the in-plane bend extending below the opening from the piercing tip to a wall of the primary needle section, whereby the piercing tip is positioned above the central axis of the biopsy needle; and
extracting the tissue sample from the biopsy region on actuation of the linear movement and the application of the negative pressure to cut the tissue sample before actuation of a rotational movement.

11. The method as claimed in claim 10, further comprising applying a pressure mechanism to collect the extracted tissue sample into a sample container, wherein the pressure mechanism is one of a suction mechanism and a fluid flushing mechanism.

12. The method as claimed in claim 10, wherein the extracting comprises:
initiating a cutting action of the biopsy needle in the biopsy region by the linear movement and initiation of the negative pressure; and terminating the cutting action by terminating both the linear movement and the application of negative pressure, and initiating the rotational motion of the biopsy needle.

13. The method as claimed in claim 10, wherein at least one of the linear movement and the rotational movement, is actuated by one of a motor and a gear mechanism.

14. The method as claimed in claim 10, wherein the at least one biopsy parameter comprises at least one of a speed of the linear movement, a speed of the rotational movement, an insertion length of the primary needle section of the biopsy needle, and a type of tissue in the biopsy region.

15. The method as claimed in claim 10, wherein the at least one biopsy parameter is determined based on an imaging technique.

* * * * *